(12) United States Patent
Okabe et al.

(10) Patent No.: US 10,882,874 B2
(45) Date of Patent: Jan. 5, 2021

(54) VANADIUM COMPOUND

(71) Applicant: ADEKA CORPORATION, Tokyo (JP)

(72) Inventors: Makoto Okabe, Tokyo (JP); Akihiro Nishida, Tokyo (JP); Tomoharu Yoshino, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 139 days.

(21) Appl. No.: 16/308,900

(22) PCT Filed: May 15, 2017

(86) PCT No.: PCT/JP2017/018235
§ 371 (c)(1),
(2) Date: Dec. 11, 2018

(87) PCT Pub. No.: WO2017/221586
PCT Pub. Date: Dec. 28, 2017

(65) Prior Publication Data
US 2019/0177346 A1    Jun. 13, 2019

(30) Foreign Application Priority Data

Jun. 22, 2016  (JP) .................................. 2016-123398

(51) Int. Cl.
| | | |
|---|---|---|
| *C07F 9/00* | (2006.01) | |
| *C23C 16/18* | (2006.01) | |
| *H01L 21/285* | (2006.01) | |
| *C07C 251/08* | (2006.01) | |
| *C23C 16/34* | (2006.01) | |
| *C23C 16/455* | (2006.01) | |

(52) U.S. Cl.
CPC ............ *C07F 9/005* (2013.01); *C07C 251/08* (2013.01); *C07F 9/00* (2013.01); *C23C 16/18* (2013.01); *C23C 16/34* (2013.01); *C23C 16/45553* (2013.01); *H01L 21/285* (2013.01)

(58) Field of Classification Search
CPC .......... C07F 9/005; C07F 9/00; C07C 251/08; C23C 16/18; C23C 16/34
See application file for complete search history.

(56) References Cited

U.S. PATENT DOCUMENTS

| | | | | |
|---|---|---|---|---|
| 4,324,736 A * | 4/1982 | Josten | ........................ | C08F 4/68 502/171 |
| 5,271,856 A * | 12/1993 | Patil | ...................... | C10M 149/14 508/281 |
| 5,278,154 A * | 1/1994 | Lacoste | ...................... | A61P 3/04 514/114 |
| 5,877,330 A * | 3/1999 | Kishimoto | ............... | B01J 23/22 502/202 |
| 6,281,378 B1 * | 8/2001 | Kishimoto | ............... | B01J 23/22 558/303 |
| 7,091,351 B2 * | 8/2006 | Dong | ...................... | A61P 35/00 546/2 |
| 9,701,764 B2 * | 7/2017 | Vallieri | ................. | C08F 210/16 |
| 2001/0055877 A1 | 12/2001 | Vaartstra | | |
| 2003/0130451 A1 * | 7/2003 | Arndt-Rosenau | ....... | C07F 9/005 526/161 |
| 2005/0020856 A1 * | 1/2005 | Bell | ...................... | C07C 309/00 562/888 |
| 2010/0270519 A1 * | 10/2010 | Blackman | ............. | C23C 16/453 252/586 |
| 2012/0315568 A1 * | 12/2012 | Lee | ..................... | H01M 4/8896 429/483 |

(Continued)

FOREIGN PATENT DOCUMENTS

| | | | | |
|---|---|---|---|---|
| EP | 0435345 A1 * | 12/1990 | ............... | C08F 4/68 |
| EP | 3 266 763 | 1/2018 | | |

(Continued)

OTHER PUBLICATIONS

Pessoa, Joao Costa, et al., "Vanadium compounds in medicine". Coordination Chemistry Reviews 301-302 (2015) pp. 24-48.*
Fernandes. Tiago A., et al., "Synthesis and catalytic properties of manganese(II) andoxovanadiunn(IV) complexes anchored to mesoporous MCM-41". Microporous and Mesoporous Materials 112 (2008) pp. 14-25.*
Gryca, Izabela, et al., "High Catalytic Activity of Vanadium Complexes in Alkane Oxidations with Hydrogen Peroxide: An Effect of 8 Hydroxyquinoline Derivatives as Noninnocent Ligands". Inorg. Chem. 2018, 57, pp. 1824-1839.*

(Continued)

*Primary Examiner* — Bret P Chen
(74) *Attorney, Agent, or Firm* — Wenderoth, Lind & Ponack, L.L.P.

(57) ABSTRACT

A vanadium compound represented by following General Formula (1).

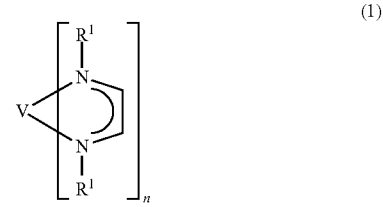

(1)

In General Formula (1), $R^1$ represents a linear or branched alkyl group having 1 to 7 carbon atoms and n represents a number from 2 to 4. $R^1$ preferably represents a secondary alkyl or a tertiary alkyl. It is preferred that in General Formula (1), n is 2 and $R^1$ is tert-butyl group or tert-pentyl group, since the compound has a broad ALD window and high thermal decomposition temperature to be able to form a good quality vanadium-containing thin film that has a small carbon residue when used as an ALD material.

3 Claims, 4 Drawing Sheets

(56) References Cited

U.S. PATENT DOCUMENTS

| | | | |
|---|---|---|---|
| 2013/0245311 A1* | 9/2013 | Nagaki | B01J 27/199 |
| | | | 560/211 |
| 2013/0251903 A1 | 9/2013 | Han | |
| 2014/0249282 A1* | 9/2014 | Vallieri | C08F 210/16 |
| | | | 526/123.1 |
| 2015/0105573 A1 | 4/2015 | Romero | |
| 2015/0126740 A1* | 5/2015 | Inoue | C07C 45/512 |
| | | | 546/7 |
| 2016/0083590 A1* | 3/2016 | Yamamoto | B05D 3/0413 |
| | | | 428/626 |
| 2017/0275312 A1* | 9/2017 | Ricci | C08F 10/06 |

FOREIGN PATENT DOCUMENTS

| | | |
|---|---|---|
| JP | 2004-323493 | 11/2004 |
| JP | 2005-023010 | 1/2005 |
| JP | 2006-511716 | 4/2006 |
| JP | 2013/545755 | 12/2013 |
| JP | 2014-534952 | 12/2014 |
| WO | 2004/046417 | 6/2004 |
| WO | 2012/027357 | 3/2012 |
| WO | 2013/046155 | 4/2013 |
| WO | 2016/203887 | 12/2016 |
| WO | 2016/204772 | 12/2016 |

OTHER PUBLICATIONS

Nomura, Kotohiro, et al., "(Imido)vanadium(V)-alkyl, -alkylidene complexes exhibiting unique reactivity towards olefins and alcohols" . Chem. Sci., 2010, 1, pp. 161-173.*

Lee, Sang-Rin, et al., "A Mechanistic Study of Vanadium-Sorbent Surface Interaction at High Temperature". Aerosol Science and Technology, 41, pp. 1063-1075, 2007.*

International Search Report dated Jun. 27, 2017 in International (PCT) Application No. PCT/JP2017/018235.

Extended European Search Report dated Nov. 22, 2019 in corresponding European Patent Application No. 17815056.1.

Database Registry (Online), Chemical Abstracts Service, Columbus, Ohio, US; Nov. 8, 2004 (Nov. 8, 2004), "Vanadium, bis(N,N-1,2-ethanedyilidenbis(2-propanamine)-dinitrosyl", XP002795465, Database accession No. 776252-18-7, with abstract.

* cited by examiner

VANADIUM COMPOUND

TECHNICAL FIELD

The present invention relates to a novel vanadium compound, a raw material for forming a thin film that includes the compound, a method for manufacturing a thin film by using the raw material for forming a thin film.

BACKGROUND ART

Thin-film materials including vanadium have been used as a barrier layer or adhesion layer for copper-containing films used for electronic materials such as LSI.

Examples of methods for manufacturing such thin films include a sputtering method, an ion plating method, a MOD method such as a coating pyrolysis method and a sol-gel method, and a chemical vapor deposition method. The chemical vapor deposition (referred to hereinbelow simply as CVD) method, inclusive of an ALD (Atomic Layer Deposition) method, is an optimum manufacturing process because it has advantages such as being suitable for mass production, excelling in composition controllability and stepwise coating ability, and enabling hybrid accumulation.

A large number of various materials have been reported as vanadium atom-supplying sources for use in the chemical vapor deposition method. For example, Patent Document 1 discloses an organovanadium compound that can be used as a raw material for forming a thin film by a MOCVD method. Further, Patent Document 2 discloses tetrakis(ethylmethylamino)vanadium that can be suitably used as a raw material for forming a thin film by a MOCVD or ALD method. Patent Documents 1 and 2 do not specifically disclose a vanadium compound according to the present invention.

Patent Document 1: Japanese Patent Application Laid Open No. 2005-023010
Patent Document 2: Japanese Patent Application Laid Open No. 2004-323493

SUMMARY OF INVENTION

Technical Problem

When a metal-containing thin film is formed on the surface of a substrate by vaporizing a raw material for chemical vapor deposition, a raw material for forming a thin film that includes absence of spontaneous combustibility and can form a high-quality thin film is suitable. In particular, a raw material for chemical vapor deposition that can be applied to an ALD method, includes absence of spontaneous combustibility and has a thermal decomposition temperature of 300° C. or more is required, since it is necessary to perform heating at 300° C. or more when using an ALD method, in order to form a high-quality thin film containing vanadium. The high-quality thin film means that that there is a small carbon residue included in the film. Tetrakis(alkylamino) vanadium that is conventionally known has a low thermal decomposition temperature and it is difficult to form a high-quality thin film containing vanadium.

Solution to the Problem

The present inventors have carried out investigations and discovered that the abovementioned problems can be solved by a specific vanadium compound, to achieve the present invention.

The present invention provides a vanadium compound represented by following General Formula (1) and a raw material for forming a thin film that includes the vanadium compound.

(1)

In the formula, $R^1$ represents a linear or branched alkyl group having 1 to 7 carbon atoms; and n represents a number of 2 to 4.

The present invention provides a method for manufacturing a thin film, comprising: introducing a vapor including a vanadium compound, which is obtained by vaporizing a raw material for forming a thin film that includes a vanadium compound represented by General Formula (1), into a film formation chamber in which a substrate is disposed; and forming, on a surface of the substrate, a thin film including vanadium atoms by inducing decomposition and/or chemical reaction of the vanadium compound.

Advantageous Effects of the Invention

In accordance with the present invention, it is possible to obtain a vanadium compound that includes absence of spontaneous combustibility and has a thermal decomposition temperature of 300° C. or more. The vanadium compound is suitable as a raw material for forming a thin film that is used for forming a metal thin film by the CVD method. Since the vanadium compound can be applied to the ALD method, it is particularly suitable as a raw material for forming a thin film by an ALD method.

DESCRIPTION OF EMBODIMENTS

The vanadium compound in accordance with the present invention is represent by General Formula (1) above. This vanadium compound is advantageous as a precursor for a thin film manufacturing method having a vaporization step, such as the CVD method. This vanadium compound can form a thin film by using the ALD method.

In General Formula (1) above, $R^1$ represents a linear or branched alkyl group having 1 to 7 carbon atoms.

Examples of the linear or branched alkyl group having 1 to 7 carbon atoms, which is represented by $R^1$ above, include methyl group, ethyl group, propyl group, isopropyl group, butyl group, isobutyl group, sec-butyl group, tert-butyl group, pentyl group, isopentyl group and hexyl group.

$R^1$ in General Formula (1) above is preferably a secondary alkyl group or a tertiary alkyl group, more preferably a tertiary alkyl group, and particularly preferably tert-butyl group or tert-pentyl group, because a temperature range that can be applied to the ALD method, called an ALD window, is broad and the thermal decomposition temperature is high.

In General Formula (1) above, n represents a number of 2 to 4. In particular, it is preferred that n is 2 because the compound has high thermal stability and it is possible to form a good vanadium-containing thin film when used as an ALD material.

It is preferred that in General Formula (1) above, n is 2 and $R^1$ is tert-butyl group or tert-pentyl group, because the compound has a broad ALD window and high thermal decomposition temperature and it is possible to form a good quality vanadium-containing thin film that has a small carbon residue when used as an ALD material. Among them, it is particularly preferred that in General Formula (1) above, n is 2 and $R^1$ is tert-butyl group, because higher effects of forming a smooth thin film with small variations in the film thickness over the entire thin film are achieved.

The preferred examples of the vanadium compound represented by General Formula (1) include compounds represented by Chemical Formulas No. 1 to No. 18 below. In Chemical Formulas No. 1 to No. 18, "Me" represents methyl group, "Et" represents ethyl group, "$^i$Pr" represents isopropyl group, "$^s$Bu" represents sec-butyl group, "$^t$Bu" represents tert-butyl group and "$^t$Am" represents tert-pentyl group.

No.1

No.2

No.3

No.4

No.5

No.6

No.7

No.8

No.9

No.10

No.11

No.12

No.13

No.14

No.15

No.16

No.17

No.18

The vanadium compound according to the present invention is not particularly restricted by the manufacturing method thereof and can be manufactured by using a well-known reaction. The vanadium compound can be manufactured, for example, by a method of conducting a reaction of an inorganic vanadium salt such as halide and nitrate, or a hydrate thereof with the corresponding diazadiene compound in the presence of a base such as sodium, lithium, sodium hydride, sodium amide, sodium hydroxide, sodium methylate, ammonia, and amines, and a method of conducting a reaction of an inorganic vanadium salt such as halide and nitrate, or a hydrate thereof with a sodium complex, a lithium complex or a potassium complex of the corresponding diazadiene compound.

The raw material for forming a thin film of the present invention includes the vanadium compound of the present invention, which has been explained hereinabove, as a precursor for the thin film, and the form of the raw material differs depending on the manufacturing process in which the raw material for forming a thin film is to be used. For example, when a thin film including only vanadium as a metal atom is manufactured, the raw material for forming a thin film of the present invention does not include metal compounds or semimetal compounds other than the vanadium compound. On the other hand, where a thin film including metals and/or semimetals of two or more types including vanadium as a metal atom is manufactured, the raw material for forming a thin film of the present invention includes, in addition to the abovementioned vanadium compound, a compound including the desired metal and/or a compound including the desired semimetal (can be also referred to hereinbelow as "other precursor"). As will be described hereinbelow, the raw material for forming a thin film of the present invention may additionally include an organic solvent and/or a nucleophilic reagent. Since physical properties of the vanadium compound serving as the precursor are advantageous for the CVD method and ALD method, the raw material for forming a thin film of the present invention is particularly useful as a raw material for chemical vapor deposition (referred to hereinbelow as "CVD").

Where the raw material for forming a thin film of the present invention is a raw material for chemical vapor deposition, the form thereof can be selected, as appropriate, according, e.g., to the delivery and feed method in the CVD method which is to be used.

The delivery and feed method can be a gas delivery method in which a CVD source is vaporized by heating and/or depressurizing the interior of a container in which the source is stored (can be referred to hereinbelow simply as "raw material container"), and the obtained vapor is introduced, optionally together with a carrier gas such as argon, nitrogen, and helium, into a film formation chamber in which a substrate is disposed (can be also referred to hereinbelow as "deposition reaction unit") or a liquid delivery method in which a CVD source is transported in a state of a liquid or solution into a vaporization chamber and vaporized by heating and/or depressurizing in the vaporization chamber, and the vapor is introduced into a film formation chamber. When the gas delivery method is used, the vanadium compound itself, which is represented by General Formula (1), can be used as the CVD source. When the liquid delivery method is used, the vanadium compound itself, which is represented by General Formula (1), or a solution obtained by dissolving the compound in an organic solvent can be used as the CVD source. Those CVD sources may additionally include the other precursor, a nucleophilic reagent or the like.

Further, CVD of a multicomponent system can be implemented by a method of vaporizing and feeding CVD sources for each component independently (can be also referred to hereinbelow as "single source method") and a method of vaporizing and feeding a mixed raw material obtained by mixing in advance multicomponent raw materials at the desired composition ratio (can be also referred to hereinbelow as "cocktail source method"). When the cocktail source method is used, a mixture of the vanadium compound of the present invention and the other precursor, or a mixed solution obtained by dissolving the mixture in an organic solvent can be used as the CVD source. The mixture or mixed solvent may additionally include a nucleophilic reagent.

The organic solvent is not particularly limited, and well-known typical organic solvents can be used. Examples of the organic solvents include acetates such as ethyl acetate, butyl acetate, and methoxyethyl acetate; ethers such as tetrahydrofuran, tetrahydropyran, ethylene glycol dimethyl ether, diethylene glycol dimethyl ether, triethylene glycol dimethyl ether, dibutyl ether, and dioxane; ketones such as methyl butyl ketone, methyl isobutyl ketone, ethyl butyl ketone, dipropyl ketone, diisobutyl ketone, methyl amyl ketone, cyclohexanone, and methylcyclohexanone; hydrocarbons such as hexane, cyclohexane, methylcyclohexane, dimethylcyclohexane, ethylcyclohexane, heptane, octane, toluene, and xylene; hydrocarbons including a cyano group such as 1-cyanopropane, 1-cyanobutane, 1-cyanohexane, cyanocyclohexane, cycanobenzene, 1,3-dicyanopropane, 1,4-dicyanobutane, 1,6-dicyanohexane, 1,4-dicyanocyclohexane, and 1,4-dicyanobenzene; pyridine and lutidine. Such organic solvents are used alone or as a mixture of two or more thereof depending on the relationship between the solute solubility, usage temperature, boiling point, and flash point. When such organic solvents are used, the amount of the entire precursor in the CVD source which is a solvent in which the precursor is dissolved in the organic solvent is preferably 0.01 mol/L to 2.0 mol/L, in particular, 0.05 mol/L to 1.0 mol/L. The amount of the entire precursor, as referred to herein, is the amount of the vanadium compound of the present invention when the raw material for forming a thin film of the present invention does not include a metal compound or a semimetal compound other than the vanadium compound of the present invention, and is the total amount of the vanadium compound of the present invention and the other precursor when the raw material for forming a thin film of the present invention includes a compound including other metal and/or a compound including a semimetal (the other precursor) in addition to the vanadium compound.

When CVD of a multicomponent system is performed, the other precursor which is used together with the vanadium compound of the present invention is not particularly limited, and any well-known typical precursor which has been used in CVD sources can be used.

Examples of the other precursor include one, or two or more compounds of silicon or a metal selected from a group including compounds having a hydride, a hydroxide, a halide, an azide, an alkyl, an alkenyl, a cycloalkyl, an aryl, an alkynyl, an amino, a dialkylaminoalkyl, a monoalkylamino, a dialkylamino, a diamine, a di(silyl-alkyl)amino, a di(alkyl-silyl)amino, a disilylamino, an alkoxy, an alkoxyalkyl, a hydrazido, a phosphido, a nitrile, a dialkylaminoalkoxy, an alkoxyalkyldialkylamino, a siloxy, a diketonate, a cyclopentadienyl, a silyl, a pyrazolate, a guanidinate, a phosphoguanidinate, an amidinate, a phosphoamidinate, a ketoiminate, a diketoiminate, a carbonyl, and a phosphoamidinate as a ligand.

Examples of metals for the precursor include magnesium, calcium, strontium, barium, radium, scandium, yttrium, titanium, zirconium, hafnium, niobium, tantalum, chromium, molybdenum, tungsten, manganese, iron, osmium, cobalt, rhodium, iridium, nickel, palladium, platinum, copper, silver, gold, zinc, cadmium, aluminum, gallium, indium, germanium, tin, lead, antimony, bismuth, lanthanum, cerium, praseodymium, neodymium, promethium, samarium, europium, gadolinium, terbium, dysprosium, holmium, erbium, thulium, and ytterbium.

Such other precursors are well known in the pertinent technical field, and the manufacturing methods thereof are also well known. For example, where an alcohol compound is used as the organic ligand, the precursor can be manufactured by conducting a reaction of the abovementioned inorganic metal salt or a hydrate thereof and the alkali metal alkoxide of the alcohol compound. Examples of the inorganic metal salt and hydrate thereof include metal halides and nitrates, and examples of the alkali metal alkoxides include sodium alkoxide, lithium alkoxide, and potassium alkoxide.

In the case of a single source method, it is preferred that the other precursor is a compound demonstrating thermal and/or oxidative decomposition behavior similar to that of the vanadium compound of the present invention. In the case of a cocktail source method, it is preferred that the precursor has similar thermal and/or oxidative decomposition behavior and also demonstrates no transformations induced by chemical reactions or the like at the time of mixing.

Compounds represented by Formulas (II-1) to (II-5) below are examples of precursors including titanium, zirconium, or hafnium among the other precursors.

In the formulas, $M^1$ represents titanium, zirconium, or hafnium; $R^a$ and $R^b$ each independently represent a $C_{1-20}$ alkyl group which may be substituted with a halogen atom and may contain an oxygen atom in a chain; $R^c$ represents a $C_{1-8}$ alkyl group; $R^d$ represents an optionally branched $C_{2-18}$ alkylene group; $R^e$ and $R^f$ each independently represent a hydrogen atom or a $C_{1-3}$ alkyl group; $R^g$, $R^h$, $R^k$, and $R^j$ each independently represent a hydrogen atom or a $C_{1-4}$ alkyl group; p represents an integer of 0 to 4; q represents 0 or 2; r represents an integer of 0 to 3; s represents an integer of 0 to 4; and t represents an integer of 1 to 4.

Examples of the $C_{1-20}$ alkyl group which may be substituted with a halogen atom and may contain an oxygen atom in a chain, this group being represented by $R^a$ and $R^b$ in Formulas (II-1) to (II-5), include methyl group, ethyl group, propyl group, isopropyl group, butyl group, sec-butyl group, tert-butyl group, isobutyl group, pentyl group, isopentyl group, neopentyl group, tert-pentyl group, hexyl group, cyclohexyl group, 1-methylcyclohexyl group, heptyl group, 3-heptyl group, isoheptyl group, tert-heptyl group, n-octyl group, isooctyl group, tert-octyl group, 2-ethylhexyl group, trifluoromethyl group, perfluorohexyl group, 2-methoxyethyl group, 2-ethoxyethyl group, 2-butoxyethyl group, 2-(2-methoxyethoxy)ethyl group, 1-methoxy-1,1-dimethylmethyl group, 2-methoxy-1,1-dimethylethyl group, 2-ethoxy-1,1-dimethylethyl group, 2-isopropoxy-1,1-dimethylethyl group, 2-butoxy-1,1-dimethylethyl group, and 2-(2-methoxyethoxy)-1,1-dimethylethyl group. The $C_{1-8}$ alkyl group as represented by $R^c$ includes methyl group, ethyl group, propyl group, isopropyl group, butyl group, sec-butyl group, tert-butyl group, isobutyl group, pentyl group, isopentyl group, neopentyl group, tert-pentyl group, hexyl group, 1-ethylpentyl group, cyclohexyl group, 1-methylcyclohexyl group, heptyl group, isoheptyl group, tert-heptyl group, n-octyl group, isooctyl group, tert-octyl group, and 2-ethylhexyl group. The optionally branched $C_{2-18}$ alkylene group which is represented by $R^d$ is a group derived from a glycol. Examples of the glycol include 1,2-ethanediol, 1,2-propanediol, 1,3-propanediol, 1,3-butanediol, 2,4-hexanediol, 2,2-dimethyl-1,3-propanediol, 2,2-diethyl-1,3-propanediol, 2,2-diethyl-1,3-butanediol, 2-ethyl-2-butyl-1,3-propanediol, 2,4-pentanediol, 2-methyl-1,3-propanediol, and 1-methyl-2,4-pentanediol. Examples of the $C_{1-3}$ alkyl group which is represented by $R^e$ and $R^f$ include methyl group, ethyl group, propyl group, and 2-propyl group. Examples of the $C_{1-4}$ alkyl group which is represented by $R^g$, $R^h$, $R^i$, and $R^k$ include methyl group, ethyl group, propyl group, isopropyl group, butyl group, sec-butyl group, tert-butyl group, and isobutyl group.

Specific examples of precursors including titanium include tetrakis(alkoxy)titanium such as tetrakis(ethoxy)titanium, tetrakis(2-propoxy)titanium, tetrakis(butoxy)titanium, tetrakis(sec-butoxy)titanium, tetrakis(isobutoxy)titanium, tetrakis(tert-butoxy)titanium, tetrakis(tert-pentyl)titanium, and tetrakis(1-methoxy-2-methyl-2-propoxy)titanium; tetrakis-β-diketonatotitanium such as tetrakis(pentane-2,4-dionato)titanium, (2,6-dimethylheptane-3,5-dionato)titanium, and tetrakis(2,2,6,6-tetramethylheptane-3,5-dionato)titanium; bis(alkoxy)bis(β-diketonato)titanium such as bis(methoxy)bis(pentane-2,4-dionato)titanium, bis(ethoxy)bis(pentane-2,4-dionato)titanium, bis(tert-butoxy)bis(pentane-2,4-dionato)titanium, bis(methoxy)bis(2,6-dimethylheptane-3,5-dionato)titanium, bis(ethoxy)bis(2,6-dimethylheptane-3,5-dionato)titanium, bis(2-propoxy)bis(2,6-dimethylheptane-3,5-dionato)titanium, bis(tert-butoxy)bis(2,6-dimethylheptane-3,5-dionato)titanium, bis(tert-amyloxy)bis(2,6-dimethylheptane-3,5-dionato)titanium, bis(methoxy)bis(2,2,6,6-tetramethylheptane-3,5-dionato)titanium, bis(ethoxy)bis(2,2,6,6-tetramethylheptane-3,5-dionato)titanium, bis(2-propoxy)bis(2,6,6,6-tetramethylheptane-3,5-dionato)titanium, bis(tert-butoxy)bis(2,2,6,6-tetramethylheptane-3,5-dionato)titanium, and bis(tert-amyloxy)bis(2,2,6,6-tetramethylheptane-3,5-dionato)titanium; and glycoxybis(β-diketonato)titanium such as (2-methylpentanedioxy)bis(2,2,6,6-tetramethylheptane-3,5-dionato)titanium and (2-methylpentanedioxy)bis(2,6-dimethylheptane-3,5-dionato)titanium; (cyclopentadienyl)tris(dialkylamino)titanium such as (methylcyclopentadienyl)tris(dimethylamino)titanium, (ethylcyclopentadienyl)tris(dimethylamino)titanium, (cyclopentadienyl)tris(dimethylamino)titanium, (methylcyclopentadienyl)tris(ethylmethylamino)titanium, (ethylcyclopentadienyl)tris(ethylmethylamino)titanium, (cyclopentadienyl)tris(ethylmethylamino)titanium, (methylcyclopentadienyl)tris(diethylamino)titanium, (ethylcyclopentadienyl)tris(diethylamino)titanium, and (cyclopentadienyl)tris(diethylamino)titanium; (cyclopentadienyl)tris(alkoxy)titanium such as (cyclopentadienyl)tris(methoxy)titanium, (methylcyclopentadienyl)tris(methoxy)titanium, (ethylcyclopentadienyl)tris(methoxy)titanium, (propylcyclopentadienyl)tris(methoxy)titanium, (isopropylcyclopentadienyl)tris(methoxy)titanium, (butylcyclopentadienyl)tris(methoxy)titanium, (isobutylcyclopentadienyl)tris(methoxy)titanium, (tert-butylcyclopentadienyl)tris(methoxy)titanium, and (pentamethylcyclopentadienyl)tris(methoxy)titanium.

Examples of precursors including zirconium or hafnium are compounds presented as examples of titanium-containing precursors in which titanium is substituted with zirconium or hafnium.

Examples of precursors including rare earth metals are compounds represented by Formulas (III-1) to (III-3).

(III-1)

(III-2)

(III-3)

In the formulas, $M^2$ represents a rare earth atom; $R^a$ and $R^b$ each independently represent a $C_{1-20}$ alkyl group which may be substituted with a halogen atom and may contain an oxygen atom in a chain; $R^c$ represents a $C_{1-8}$ alkyl group; $R^e$ and $R^f$ each independently represent a hydrogen atom or a $C_{1-3}$ alkyl group; $R^g$ and $R^j$ each independently represent a $C_{1-4}$ alkyl group; p' represents an integer of 0 to 3; and r' represents an integer of 0 to 2.

Examples of rare earth atoms represented by $M^2$ in the precursor including a rare earth element include scandium, yttrium, lanthanum, cerium, praseodymium, neodymium, promethium, samarium, europium, gadolinium, terbium, dysprosium, holmium, erbium, thulium, ytterbium, and lutetium. Examples of groups represented by $R^a$, $R^b$, $R^c$, $R^e$, $R^f$, $R^g$, and $R^j$ include groups presented by way of examples with respect to the titanium-containing precursors.

If necessary, the raw material for forming a thin film of the present invention may include a nucleophilic reagent to stabilize the vanadium compound of the present invention and the other precursor. Examples of the nucleophilic reagent include ethylene glycol ethers such as glyme, diglyme, triglyme, and tetraglyme; crown ethers such as 18-crown-6, dicyclohexyl-18-crown-6, 24-crown-8, dicyclohexyl-24-crown-8, and dibenzo-24-crown-8; polyamines such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, 1,1,4,7,10,10-hexamethyltriethylenetetramine, and triethoxytriethyleneamine; cyclic polyamines such as cyclam and cyclen; heterocyclic compounds such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole, and oxathiolane; β-keto esters such as methyl acetoacetate, ethyl acetoacetate, and 2-methoxyethyl acetoacetate; and β-diketones such as acetylacetone, 2,4-hexanedione, 2,4-heptanedione, 3,5-heptanedione, and dipivaroylmethane. These nucleophilic reagents are used in an amount preferably within a range of 0.1 mol to 10 mol, more preferably 1 mol to 4 mol per mole of the amount of the entire precursor.

In the raw material for forming a thin film of the present invention, the amount of metal element impurities, halogen impurities such as chlorine-containing impurities, and organic impurities, which are different from the components constituting the raw materials, needs to be minimized. The content of the metal element impurities is preferably 100 ppb or less, and more preferably 10 ppb or less for each element, and the total amount of the impurities is preferably 1 ppm or less, and more preferably 100 ppb or less. In particular, when the raw material is used to form a gate insulating layer, a gate film, or a barrier layer of an LSI, it is necessary to reduce the amount of alkali metal elements and alkaline earth metal elements which affect the electric properties of a thin film to be obtained. The amount of the halogen impurities is preferably 100 ppm or less, more preferably 10 ppm or less, and most preferably 1 ppm or less. The total amount of organic impurities is preferably 500 ppm or less, more preferably 50 ppm or less, and most preferably 10 ppm or less. Since moisture causes particle generation in the raw material for chemical vapor deposition or particle generation during thin film formation, it is better to remove moisture as much as possible prior to use from the precursor, the organic solvent, and the nucleophilic reagent in order to reduce the amount of moisture therein. The amount of moisture in each of the precursor, the organic solvent, and the nucleophilic reagent is 10 ppm or less, and more preferably 1 ppm or less.

Further, in order to reduce or prevent the particle contamination of the thin film to be formed, it is preferred that the raw material for forming a thin film of the present invention include as few particles as possible. More specifically, in particle measurements with a particle detector of a light scattering type in a liquid phase, the number of particles larger than 0.3 µm is preferably 100 or less in 1 ml of the liquid phase, more preferably the number of particles larger than 0.2 n is 1000 or less in 1 ml of the liquid phase, and most preferably the number of particles larger than 0.2 µm is 100 or less in 1 ml of the liquid phase.

A method for manufacturing a thin film of the present invention by which a thin film is manufactured by using the raw material for forming a thin film of the present invention is based on the CVD method in which a vapor produced by vaporizing the raw material for forming a thin film of the present invention, and an optionally used reactive gas are introduced into a film formation chamber in which a substrate is disposed, and the precursor is then decomposed and/or chemically reacted on the substrate to grow and deposit a thin film including a metal on the substrate surface. The method for delivering and feeding the raw materials, the deposition method, manufacturing conditions, and manufacturing apparatus are not particularly restricted, and well-known typical conditions and methods can be used.

Examples of the optionally used reactive gas include oxidative gases such as oxygen, ozone, nitrogen dioxide, nitrogen monoxide, water vapor, hydrogen peroxide, formic acid, acetic acid, and acetic anhydride; reductive gases such as hydrogen; and gases producing nitrides, for example, organic amine compounds such as monoalkylamines, dialkylamines, trialkylamines, and alkylenediamines, hydrazine, and ammonia. These gases can be used individually or in combinations of two or more thereof.

Examples of the delivery and feeding methods include the above-described gas delivery method, liquid delivery method, single source method, and cocktail source method.

Examples of the deposition method include thermal CVD in which a source gas or a source gas and a reactive gas are reacted only by heat in order to deposit a thin film; plasma CVD in which heat and plasma are used; photo-excited CVD in which heat and light are used; photo- and plasma-excited CVD in which heat, light and plasma are used; and ALD in which the CVD deposition reaction is separated into elementary steps and deposition is performed step by step at a molecular level.

Examples of the substrate material include silicon, ceramics such as silicon nitride, titanium nitride, tantalum nitride, titanium oxide, titanium nitride ruthenium oxide, zirconium oxide, hafnium oxide, and lanthanum oxide; glass; and metals such as metallic ruthenium. The substrate may be in the form of a sheet, sphere, fibers, and flakes. The substrate surface may be flat or may have a three-dimensional structure such as a trench structure.

The manufacturing conditions include the reaction temperature (substrate temperature), reaction pressure, deposition rate, and the like. The reaction temperature is preferably 100° C. or higher, at which the vanadium compound of the present invention is sufficiently reactive, and more preferably 150° C. to 500° C. Since the vanadium compound of the present invention has a thermal decomposition temperature of 300° C. or more, the reaction temperature is particularly preferably 250° C. to 450° C. The reaction pressure is preferably from atmospheric pressure to 10 Pa for thermal CVD and photo-excited CVD, and preferably from 2000 Pa to 10 Pa when plasma is used.

The deposition rate can be controlled by the raw material feed conditions (vaporization temperature and vaporization pressure), reaction temperature, and reaction pressure. Since a high deposition rate can degrade the properties of the resulting thin film and a low deposition rate can cause problems with productivity, the deposition rate is preferably 0.01 nm/min to 100 nm/min and more preferably 1 nm/min to 50 nm/min. In the ALD method, the control is performed by the number of cycles so as to obtain the desired film thickness.

The temperature or pressure during vaporization of the raw material for forming a thin film can be also considered as the manufacturing condition. The step of obtaining the vapor by vaporizing the raw material for forming a thin film may be performed inside the raw material container or inside the vaporization chamber. In either case, it is preferred that the raw material for forming a thin film of the present invention be evaporated at 0° C. to 150° C. Further, where the raw material for forming a thin film is vaporized to obtain the vapor inside the raw material container or vaporization chamber, it is preferred that the pressure inside the raw material container and the pressure inside the vaporization chamber be 1 Pa to 10,000 Pa.

The method for manufacturing a thin film of the present invention, when it is realized by the ALD method, may include a raw material introduction step in which the raw material for forming a thin film is vaporized to obtain a vapor and the vapor is introduced into the film formation chamber by the abovementioned delivery and feeding method, and also a precursor thin film formation step of forming a precursor thin film on the surface of the substrate with the vanadium compound in the vapor, an evacuation step of evacuating the unreacted vanadium compound gas, and a vanadium-containing thin film formation step of chemically reacting the precursor thin film with a reactive gas and forming a thin film including vanadium atoms on the surface of the substrate.

Each of the abovementioned steps will be described hereinbelow in greater detail with reference to the case of forming a vanadium nitride thin film. When a vanadium nitride thin film is formed by the ALD method, initially, the raw material introduction step, which has been explained hereinabove, is performed. The temperature and pressure preferred when vaporizing the raw material for forming a thin film are the same as explained hereinabove. Then, a precursor thin film is formed on the substrate surface with the vanadium compound introduced in the deposition reaction unit (precursor thin film formation step). At this time, heat may be applied by heating the substrate or heating the deposition reaction unit. The precursor thin film which is formed in this step is a vanadium oxide thin film or a thin film generated by decomposition and/or reaction of part of the vanadium compound and has a composition different from the target vanadium nitride thin film. The substrate temperature employed in this step is preferably from room temperature to 500° C., more preferably from 200° C. to 500° C. The pressure in the system (in the film formation chamber) when this step is performed is preferably 1 Pa to 10000 Pa, more preferably 10 Pa to 1000 Pa.

The unreacted vanadium compound gas and byproduct gas are then evacuated from the deposition reaction unit (evacuation step). The unreacted vanadium compound gas and byproduct gas are ideally completely evacuated from the deposition reaction unit, but such complete evacuation is not always necessary. Examples of the evacuation method include a method of purging the interior of the system with an inactive gas such as nitrogen, helium, and argon, a method of evacuating by depressurizing the interior of the system, and a method in which the aforementioned methods are combined. The degree of depressurization when the depressurization method is used is preferably 0.01 Pa to 300 Pa, more preferably 0.01 Pa to 100 Pa.

The reactive gas such as ammonia gas is then introduced into the deposition reaction unit and a vanadium nitride thin film is formed from the precursor thin film, which has been formed in the preceding precursor thin film formation step, under the action of the reactive gas or the action of the reactive gas and heat (vanadium nitride-containing thin film formation step). The temperature when heat is used in this step is preferably from room temperature to 500° C., more preferably from 150° C. to 350° C. The pressure in the system (in the film formation chamber) in which this step is performed is preferably 1 Pa to 10000 Pa, more preferably 10 Pa to 1000 Pa. The vanadium compound of the present invention has good reactivity with reactive gases such as ammonia gas and can yield a vanadium nitride thin film. Further, the vanadium compound of the present invention has good reactivity with oxidizing gases such as ozone and can also yield a vanadium oxide thin film.

When the ALD method is used in the above-described manner in the method for manufacturing a thin film of the present invention, thin film deposition performed by a series of operations including the raw material introduction step, precursor thin film formation step, evacuation step, and vanadium nitride-containing thin film formation step may be taken as one cycle, and such cycles may be repeated a plurality of times till a thin film of a necessary thickness is obtained. In this case, after one cycle is completed, it is preferred that the unreacted vanadium compound gas, reactive gas (ammonia gas and the like when a vanadium nitride thin film is formed), and byproduct gas be evacuated from the deposition reaction unit in the same manner as in the evacuation step, and the next cycle be thereafter performed.

When a vanadium nitride thin film is formed by the ALD method, energy such as plasma, light, and voltage may be applied, and a catalyst may be used. The time period for applying the energy and the time period for using the catalyst are not particularly limited. For example, the energy may be applied and the catalyst may be used when the vanadium compound gas is introduced in the raw material introduction step, during heating in the precursor thin film formation step or vanadium nitride-containing thin film formation step, during evacuation of the interior of the system in the evacuation step, when the reactive gas such as ammonia gas is introduced in the vanadium nitride-containing thin film formation step, and also between the aforementioned steps.

Further, in the method for manufacturing a thin film of the present invention, annealing may be performed under an inactive gas atmosphere, an oxidizing atmosphere, or a reducing atmosphere after the thin film deposition to obtain better electric properties, and a reflow step may be employed when bump embedding is needed. In this case, the temperature is 200° C. to 1000° C., preferably 250° C. to 500° C.

Figure 1:
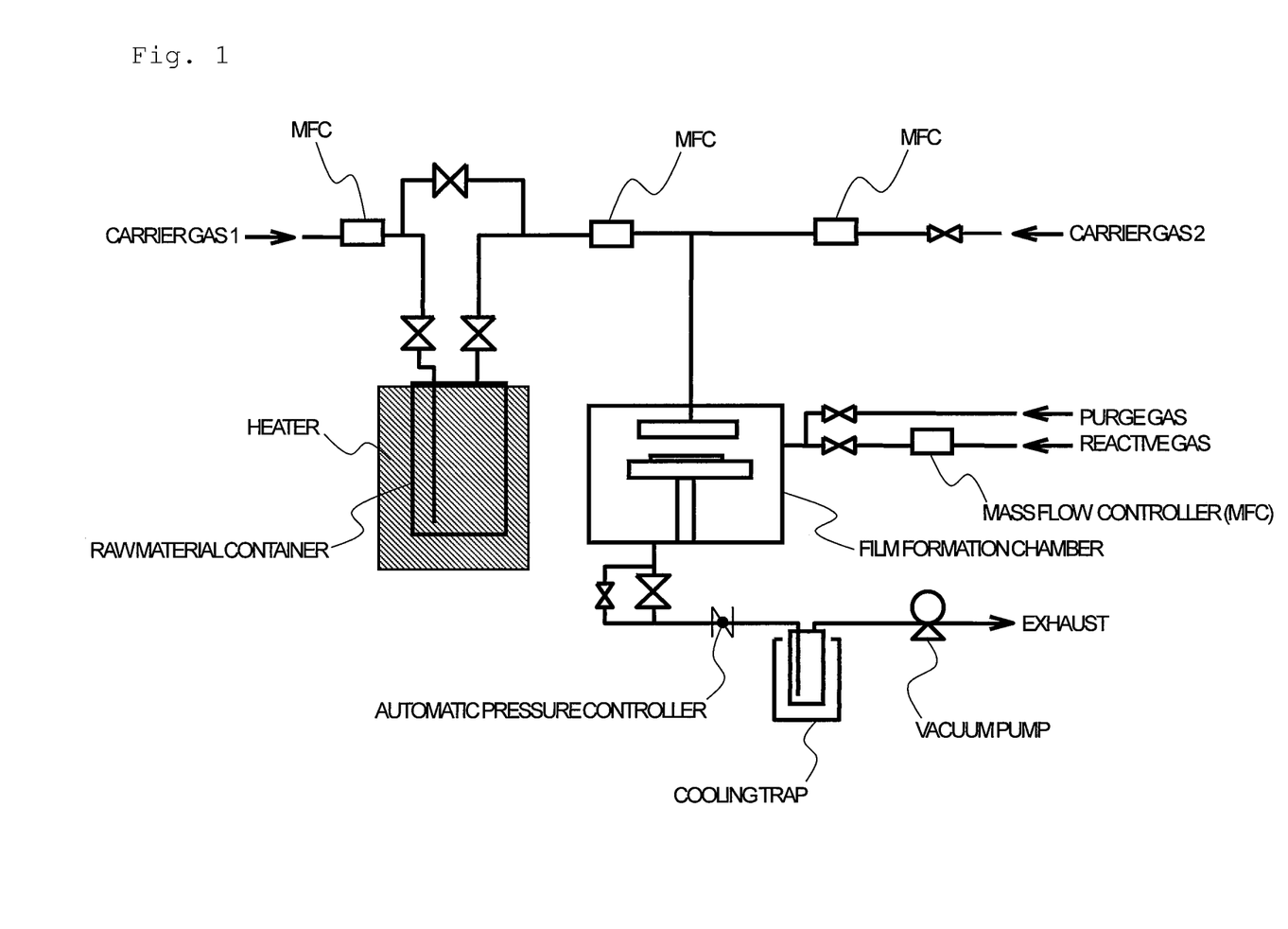
FIG. 1 is a conceptual diagram illustrating an example of a chemical vapor deposition apparatus for use in the method for manufacturing a thin film in the present invention.
Figure 2:
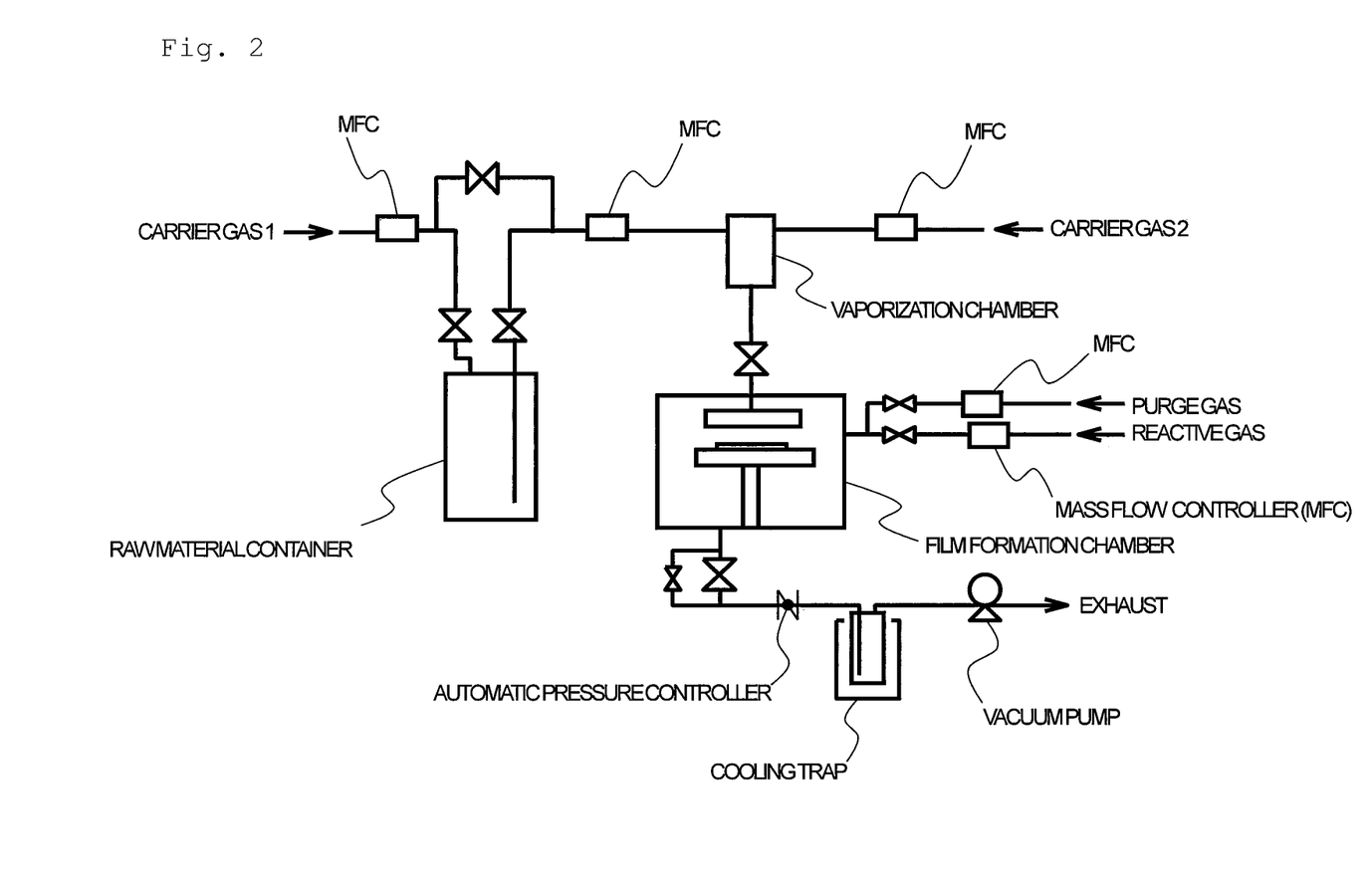
FIG. 2 is a conceptual diagram illustrating another example of a chemical vapor deposition apparatus for use in the method for manufacturing a thin film in the present invention.
Figure 3:
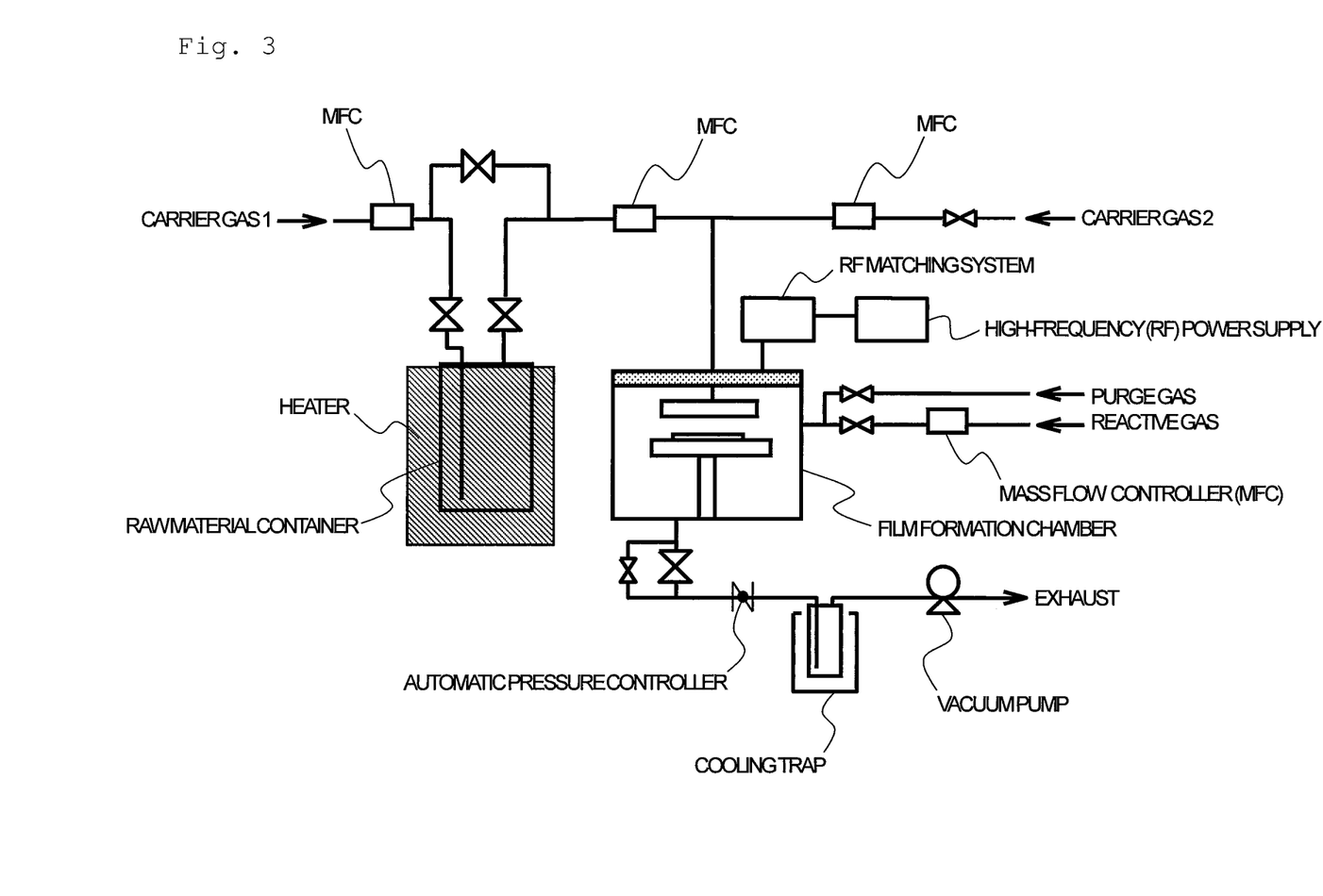
FIG. 3 is a conceptual diagram illustrating another example of a chemical vapor deposition apparatus for use in the method for manufacturing a thin film in the present invention.
Figure 4:
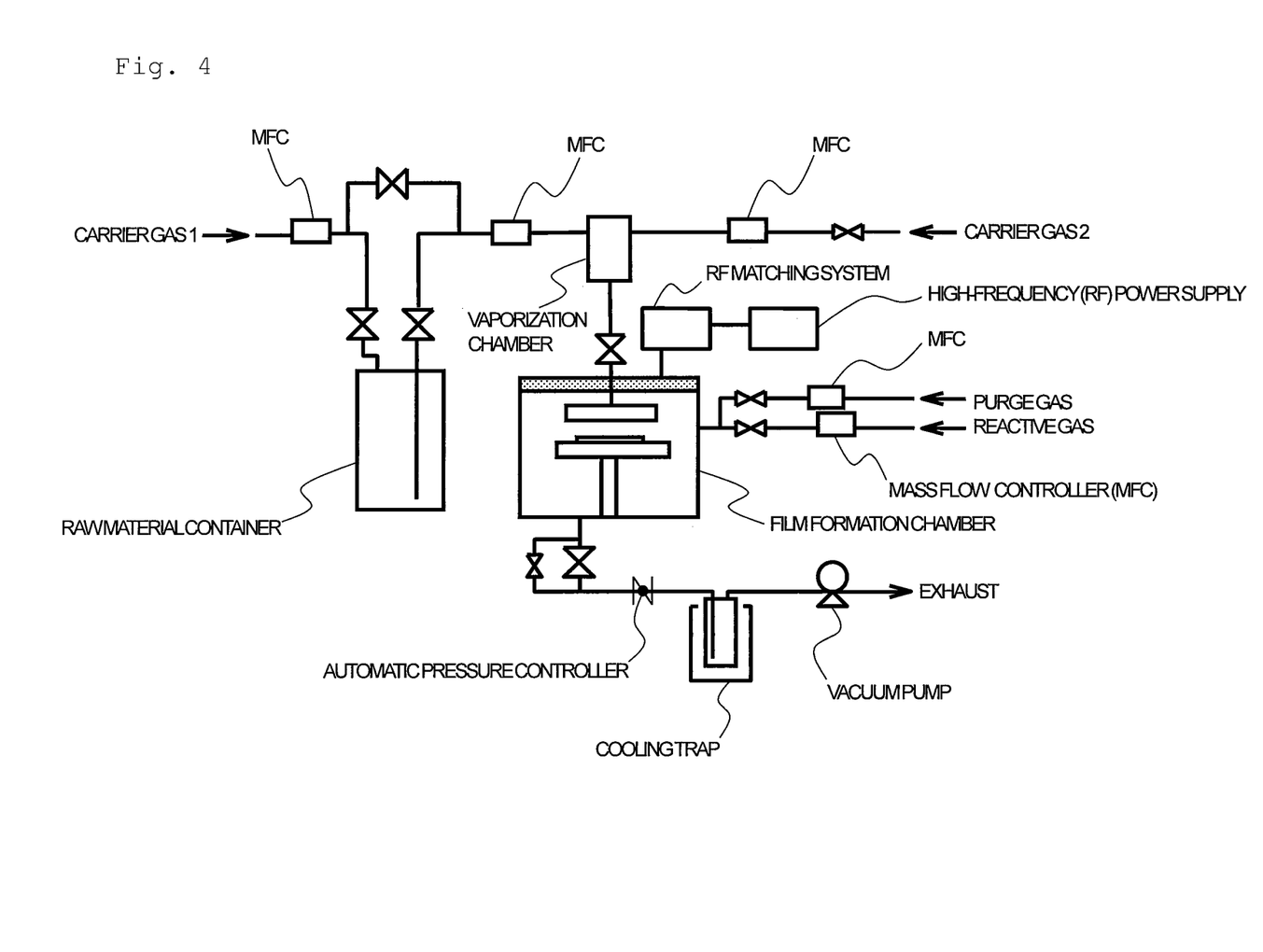
FIG. 4 is a conceptual diagram illustrating another example of a chemical vapor deposition apparatus for use in the method for manufacturing a thin film in the present invention.

A well-known chemical vapor deposition apparatus can be used for manufacturing a thin film by using the raw material for forming a thin film of the present invention. Specific examples of suitable apparatuses include an apparatus, such as depicted in FIG. 1, in which a precursor can be fed by bubbling, and an apparatus, such as depicted in FIG. 2, which has a vaporization chamber. An apparatus can be also used in which, as depicted in FIG. 3 and FIG. 4, plasma treatment can be performed with respect to a reactive gas. The single-substrate apparatuses, such as depicted in FIG. 1 to FIG. 4, are not limiting, and an apparatus which uses a batch furnace and is capable of simultaneous processing of a large number of substrates can be also used.

Where a thin film is manufactured using the raw material for forming a thin film of the present invention, the desired type of thin film such as metal, oxide ceramic, and nitride ceramic can be formed by appropriately selecting the other precursor, reactive gas, and manufacturing conditions. Such thin films are known to exhibit various electric properties, optical properties and the like, and are used for a variety of applications. For example, such thin films are used as a barrier layer or adhesion layer for copper-containing films used for electronic materials such as LSI.

EXAMPLES

The present invention will be explained hereinbelow in greater detail with reference to Examples and Evaluation Examples. However, the present invention is not limited by the Examples, etc., below.

Example 1: Synthesis of Compound No. 5

10.2 g (0.0646 mol) of vanadium (III) chloride and 52 g of tetrahydrofuran were loaded into a 300 ml 4-necked flask, and stirred at room temperature. A solution prepared by dissolving 32.6 g (0.194 mol) of N,N'-di-tert-butyl-1,4-diaza-1,3-butadiene and 1.35 g (0.194 mol) of lithium in 110 g of tetrahydrofuran was added dropwise thereto at a liquid temperature of from −20 to −15° C. cooled with a dry ice-isopropanol. After the end of the dropping, the mixture was stirred under heating at 80° C. Thereafter, a solvent was removed at 60° C. in an oil bath under a slightly reduced pressure. The residue was dissolved into toluene and then filtered. The solvent was removed from the obtained toluene solution at 100° C. in an oil bath under a reduced pressure. The residue was purified by a distillation under the conditions of 20 Pa and 160° C. to obtain a target product. The yield was 17.1 g, and the percentage yield was 68.4%. Spontaneous combustion was checked with respect to the obtained target product by allowing the product to stay in the air. There was no spontaneous combustion.

(Analytical Data)
(1) Elemental Analysis
V: 13.0 mass %, C: 61.1 mass %, H: 11.1 mass %, N: 14.4 mass %
(theoretical values V: 13.1 mass %, C: 61.4 mass %, H: 11.3 mass %, N: 14.3 mass %)
(2) Normal-Pressure TG-DTA
Temperature of 50% mass reduction: 231° C. (Ar flow rate: 100 ml/min; temperature increase rate 10° C./min)
(3) Reduced-Pressure TG-DTA
Temperature of 50% mass reduction: 151° C. (10 Torr, Ar flow rate: 50 ml/min; temperature increase rate 10° C./min)

Example 2: Synthesis of Compound No. 6

3.54 g (0.0225 mol) of vanadium (III) chloride and 20 g of tetrahydrofuran were loaded into a 300 ml 4-necked flask, and stirred at room temperature. A solution prepared by dissolving 13.3 g (0.0675 mol) of N,N'-di-tert-amyl-1,4-diaza-1,3-butadiene and 0.47 g (0.0675 mol) of lithium in 30 g of tetrahydrofuran was added dropwise thereto at a liquid temperature of from −20 to −15° C. cooled with a dry ice-isopropanol. After the end of the dropping, the mixture was stirred under heating at 80° C. Thereafter, a solvent was removed at 60° C. in an oil bath under a slightly reduced pressure. The residue was dissolved into toluene and then filtered. The solvent was removed from the obtained toluene solution at 100° C. in an oil bath under a reduced pressure. The residue was purified by a distillation under the conditions of 15 Pa and 125° C. to obtain a target product. The yield was 3.56 g, and the percentage yield was 35.6%. Spontaneous combustion was checked with respect to the obtained target product by allowing the product to stay in the air. There was no spontaneous combustion.

(Analytical Data)
(1) Elemental Analysis
V: 11.6 mass %, C: 64.5 mass %, H: 10.9 mass %, N: 12.4 mass %
(theoretical values V: 11.5 mass %, C: 64.4 mass %, H: 11.7 mass %, N: 12.5 mass %)
(2) Normal-Pressure TG-DTA
Temperature of 50% mass reduction: 263° C. (Ar flow rate: 100 ml/min; temperature increase rate 10° C./min)
(3) Reduced-Pressure TG-DTA
Temperature of 50% mass reduction: 180° C. (10 Torr, Ar flow rate: 50 ml/min; temperature increase rate 10° C./min)

[Evaluation Example 1] Evaluation of Thermal Stability

Thermal stability of Compounds No. 5 and 6 and Comparative Compound 1 shown below were checked by measuring the temperature at which an exothermic peak was observed as a thermal decomposition temperature by using a DSC measurement device. The results are shown in Table 1.

Comparative Compound 1

TABLE 1

|  |  | Thermal decomposition temperature |
| --- | --- | --- |
| Evaluation example 1-1 | Compound No. 5 | 320° C. |
| Evaluation example 1-2 | Compound No. 6 | 315° C. |
| Evaluation example 1-3 | Comparative Compound 1 | 270° C. |

It can be seen from Table 1 above that Comparative Example 1 has a thermal decomposition temperature less than 300° C. On the other hand, Compounds No. 5 and No. 6 have a thermal decomposition temperature of 300° C. or more. The higher a thermal decomposition temperature of a compound is, the higher a thermal stability is. When thermal stability of a compound as a raw material for forming a thin film is high, the film can be formed at a higher temperature. The possibility of forming a film at a higher temperature means that the amount of impurities, such as carbon residue, contained in the obtained thin film can be reduced. Therefore, thermal stability of a compound as a raw material for forming a thin film affects the quality of the thin film which is to be obtained.

[Example 3] Manufacture of Thin Film of Vanadium Nitride by ALD Method

Compound No. 5 or 6 was used as a raw material for chemical vapor deposition, and a thin film of vanadium nitride was manufactured on a silicon substrate by the ALD method under the below-described conditions by using the ALD apparatus depicted in FIG. 1. Regarding the obtained thin film, the thickness was measured by an X-ray reflectance method, and the thin film structure and thin film composition were verified by an X-ray diffraction method and an X-ray photoelectron spectroscopy. The film thickness was 3 nm to 6 nm, and the composition of the thin film was vanadium nitride (confirmed by V2p and N1s peaks in XPS analysis). The amount of carbon was less than the lower detection limit of 0.1 atom %. The film thickness obtained per one cycle was 0.02 nm to 0.04 nm. Further, when the cross-section of the obtained vanadium nitride thin film was observed, the thin film manufactured by using Compound No. 5 had a very small variation in the film thickness of the entire thin film, as compared with the thin film manufactured by using Compound No. 6.

(Conditions)

Reaction temperature (substrate temperature): 320° C., Reactive gas: ammonia gas (Steps)

The series of the following steps (1) to (4) was taken as 1 cycle, and 150 cycles were performed.

(1) The vapor of a raw material for chemical vapor deposition that is vaporized under the conditions of a raw material container heating temperature of 70° C. and a raw material container pressure of 100 Pa is introduced, and deposition is performed for 30 seconds under a system pressure of 100 Pa.

(2) The unreacted raw material is removed by purging with argon for 10 seconds.

(3) A reactive gas is introduced and the reaction is conducted for 30 seconds under a system pressure of 100 Pa.

(4) The unreacted raw material is removed by purging with argon for 10 seconds.

[Comparative Example 2] Manufacture of Thin Film of Vanadium Nitride by ALD Method

A thin film of vanadium nitride was manufactured in a manner similar to Example 3, except that Comparative Compound 1 was used. As a result, the amount of carbon in the vanadium-containing thin film formed on the silicon substrate was 20 atom % or more.

The results of Example 3 show that a good-quality thin film of vanadium nitride can be obtained by the ALD method. On the other hand, the result of Comparative Example 2 shows that a high-quality thin film of vanadium nitride cannot be obtained.

The present international application claims priority from Japanese Patent Application No. 2016-123398 filed on Jun. 22, 2016, the full contents whereof are incorporated herein by reference.

The invention claimed is:

1. A vanadium compound represented by following Formula (1):

wherein $R^1$ represents a linear or branched alkyl group having 1 to 7 carbon atoms; and n represents a number from 2 to 4.

2. A raw material for forming a thin film, comprising the compound according to claim 1.

3. A method for manufacturing a thin film, comprising: introducing a vapor including a vanadium compound obtained by vaporizing the raw material for forming a thin film according to claim 2 into a film formation chamber in which a substrate is disposed; and forming, on a surface of the substrate, a thin film including vanadium atoms by inducing decomposition and/or chemical reaction of the vanadium compound.

* * * * *